United States Patent [19]

Myerson

[11] Patent Number: 5,501,836
[45] Date of Patent: Mar. 26, 1996

[54] ENTRAPPED NON-ENZYMATIC MACROMOLECULES FOR CHEMICAL SENSING

[75] Inventor: Joel Myerson, Berkely, Calif.

[73] Assignee: Hewlett Packard Company, Palo Alto, Calif.

[21] Appl. No.: 273,384

[22] Filed: Jul. 11, 1994

[51] Int. Cl.[6] ................................................. G01N 21/17
[52] U.S. Cl. .................... 422/57; 422/82.05; 436/166; 525/54.1
[58] Field of Search .............................. 422/82.05, 82.06, 422/82.07, 82.08, 82.09, 82.11, 57; 525/54.1; 436/166

[56] References Cited

U.S. PATENT DOCUMENTS

| | | | |
|---|---|---|---|
| 5,047,350 | 9/1991 | Switalski et al. | 436/136 |
| 5,292,801 | 3/1994 | Avnir et al. | 525/54.1 |
| 5,300,564 | 4/1994 | Avnir et al. | 525/54.1 |

*Primary Examiner*—Jeffrey R. Snay
*Attorney, Agent, or Firm*—Deborah A. Neville

[57] ABSTRACT

A sensor made of porous matrix or sol-gel glass and non-enzymatic macromolecular polymer immobilized in the sol-gel glass. The macromolecule is physically entangled or otherwise trapped, and does not leach regardless of exposure to elevated temperature and pressure. Surface effects are minimized since the there is no chemical bond between macromolecules and sol-gel glass. Indicator molecules may be attached to the macromolecular polymer either before or after the macromolecule is incorporated into the porous matrix.

4 Claims, No Drawings

ENTRAPPED NON-ENZYMATIC MACROMOLECULES FOR CHEMICAL SENSING

BACKGROUND OF THE INVENTION

1. Field of the Invention

This invention relates to chemical sensors, more particularly, to a method of making a indicator attached to a macromolecule immobilized in sol-gel glass. The immobilized macromolecule is entangled in the sol-gel so that even temperatures experienced during autoclaving do not cause the macromolecule or the indicator to leach or otherwise separate from the sol-gel glass.

2. Description of Related Art

Chemical sensors, in order to be reliable, reproducible and practical, usually require that whatever chemistry is incorporated into the sensor does not leach out into the surrounding matrix. Leaching can degrade the sensor's performance as well as contaminate the sample. Typically this problem has been addressed by covalently bonding molecules of interest to a solid support, or creating a polymer in which the molecule of interest is incorporated into the polymer matrix during the polymerization process. In the case of optically based sensors, the optical properties of the support are also important.

Sol-gel glasses have been used as a basis for chemical sensors. Sol-gel glass is an optically transparent amorphous silica or silicate material produced by forming interconnections in a network of colloidal, submicrometer particles under increasing viscosity until the network becomes completely rigid, with about one-half the density of glass. (For a comprehensive text, readers may refer to *Sol Gel Science* by Jeffrey C. Brinker and George W. Scherer, Academic Press, Inc., San Diego, 1990.)

The sol-gel process comprises hydrolysis and condensation of starting monomers to produce a colloidal suspension (the "sol"), gelation (to form a wet network of porous metal oxide), and drying (and shrinking) to form the "xerogel" (i.e. dry gel); final sintering (optional) at elevated temperature densities the xerogel into pore-free glass. A general discussion of sol-gel porous glass technology can be found in "Diagnostic Applications of Organically Doped Sol-Gel Porous Glass", O Lev, *Analusis*, 1992, v20, N9 (Nov), p543–553. Typically, the sol-gel process begins with soluble precursors. Usually these are metal-organic derivatives such as tetramethoxysilane (TMOS) or tetraethoxysilane (TEOS), which react with water to form extremely small colloidal structures that comprise the sol. While mixing the liquid precursor with the water, a hydrolysis reaction occurs. The hydrated silica immediately interacts in a condensation reaction forming Si—O—Si bonds.

Linkage of additional Si—OH tetrahedra occurs as a polycondensation reaction, eventually resulting in a $SiO_2$ network. Hydrolysis and polycondensation reactions initiate at numerous sites within the TMOS or TEOS aqueous solution as mixing occurs. When sufficient interconnected Si—O—Si bonds are formed in a region they respond cooperatively as a colloidal (submicron) particle, or pre-network. The suspension of these colloidal particles in their parent liquid is termed a sol. The sol still behaves as a low-viscosity liquid and can be cast into a mold.

After casting into a mold, gelation occurs: the colloidal particles link together to become a three-dimensional network. When gelation occurs, viscosity increases sharply and a solid results. Aging of a gel involves keeping the gel immersed for some period of time (hours to days), during which time the gel decreases in porosity and develops the strength necessary to resist cracking during drying (curing).

During drying, the pore liquid is removed and evaporation is controlled to avoid stress cracks. The density of dried gels ranges from as low as 5% of the density of a melt-derived material to as much as 60% of theoretical density. Low-density gels are called aerogels; high density gels are xerogels.

The sol-gel glass is optically transparent but contains a large fraction of interconnected pores. Small indicator molecules of various kinds can be incorporated into the porous matrix during the formation of the sol-gel. Because the molecules are small, they tend to diffuse out of the glass, particularly at elevated temperatures.

The sol-gel technique has also been shown as a way to immobilize enzymes. A biosensor can be made by entrapping the enzyme in the porous matrix during the formation of the xerogel. The enzyme remains active and resistant to leaching, being physically trapped or entangled in the three-dimensional silica structure created during the sol-gel process. Enzymes are limited by a number of characteristics, including temperature and solvent sensitivity, because such sensitivities restrict the applications of enzyme-based sensors.

Leaching has been a persistent problem in chemical sensors irrespective of the formation technique. Unless prevented, molecules can (and generally do) leach off the matrix support. Covalent attachment of indicator molecules has been used to prevent indicator leaching, as well as to prevent the changes resulting from leaching, such as changes in the surface concentration of indicator and the contamination of the surrounding liquid. Typically, one derivatizes a surface such that pendant groups can then be reacted and bonded covalently with the indicator molecules. For example, aminopropyltriethoxylane can be reacted with a silica surface to form "amino-propyl silica." The pendant amino groups can be reacted with a carboxyl group on the indicator molecule to form a stable amide bond.

Sensors based on the incorporation of small indicator molecules into a sol-gel glass can also be unstable due to the leaching of the indicator. Leaching is especially problematic if the sensor is exposed to high temperatures. Smaller pore sizes slow the leaching process but, at least in block sensors, have the undesirable characteristic of retarding the response time of the sensor, since response time is a function of the rate of diffusion. Sol-gels made as thin films, however have small pores and faster response times because diffusion remains rapid.

Enzymes, by virtue of being entangled or otherwise immobilized in the sol-gel, do not present the same leaching problem as small indicator molecules but, rather, pose other difficulties. Although entangled enzymes offer the possibility of very sensitive and specific analyses, enzymes are not suited for all applications. Enzymes have limited lifetimes, are sensitive to solvents, and are not stable at the temperatures required for sterilization.

Surface Design Characteristics

Control of surface density of reactive groups is an ongoing challenge. Typically, the surface density of amino groups is no greater than 500 micromoles per gram of support, which has the practical effect of limiting the amount of indicator that can be bound to the surface. Controlling both the amount and mixture of reactive groups is difficult; even if accomplished, the density of reactive groups affixed to a sensor is difficult to measure.

Optical properties of supporting matrices and surface effects arising out of interactions between the indicator molecules and the support substrate have also remained significant obstacles to designing stable, useful sensors. Many porous supports that are typically used are not optically clear and cause light to scatter, thereby constraining sensor design.

Covalent bonding of indicator molecules to the sol-gel glass is one remedy for the leaching problem. Covalent bonding requires a degree of surface preparation that drives up the cost associated with sensor manufacturing. Covalent bonding does not allow controlled mixing of multiple indicators; nor does it afford the degree of control over the surface environment that is often desirable (e.g., hydrophilic or hydrophobic sensor areas).

Moreover, covalent bonding often creates undesirable surface effects because the indicator is so close to the surface that it responds to the microenvironment of the substrate surface rather than to the general environment that it is designed to "sense". Surface effects can play a dominant role in the behavior of any chemistry that involves the groups that are covalently bound. In some instances, the use of linker molecules to extend off the surface of the solid support helps to partially alleviate this problem, but surface effects can still predominate and interfere with the indicator performance.

As demonstrated by the foregoing, there is a need for sensors that do not have the limitations of enzymes or of current commercially available small-molecule sensors. That is to say, there is a need for sensors that are stable at temperatures above 100 degrees C. and that remain stable for months or longer. It is further desirable that such a sensor be non-leaching. Moreover, a sensor with high concentrations of bound indicator but without the interference of surface effects is also desirable. Also needed is a sensor that may be custom designed according to size, shape and composition specifications.

SUMMARY OF THE INVENTION

The invention provides a sensor in which a non-enzymatic macromolecule is immobilized, by entanglement or entrapment or some other means, in a sol-gel glass. Since the non-enzymatic macromolecule is physically entangled by means of the sol-gel matrix forming around and entangling portions of the macromolecule there is no leaching (even if exposed to temperatures of 121 degree C. or above); sensor performance is robust and can withstand exposure to solvents. In some embodiments the invention provides that smaller indicator molecules may be covalently attached to the nonenzymatic macromolecules. However, since there is no covalent bonding between the sol-gel and the non-enzymatic macromolecule, surface effects are minimized. The indicator will respond to changes in the surrounding solution rather than have sensitivity impaired as a result of surface effects. Alternatively, the indicator may be designed to respond to an additional polymer within the sol-gel as if the additional polymer were the sol-gel surface.

The invention provides for control of the local environment of the indicator molecules. By incorporating neutral or charged non-indicating macromolecules, physical parameters such as ionic strength or permeability can be controlled. The invention provides for flexibility in design and control of indicator concentration. "Custom" indicators with several types of indicators in pre-selected ratios on a single matrix may be designed according to the invention. Moreover, the invention provides a sensor that may contain higher concentrations of indicator molecules or material with greater densities of reactive groups than could be accomplished by surface derivitization.

The invention provides a sol-gel glass that is optically clear and that can be customized as to size, shape and surface characteristics, and may be cast as a film. The sol-gel glass may be custom designed with monomers (e.g., charged or hydrophobic) in order to exert additional control over the physical properties of the sensor.

The method of manufacturing a sensor element according to the invention provides that the indicator molecules attached to a macromolecule (a polymer chain) and then incorporated into the sol-gel. Alternatively, the macromolecules may be incorporated into the porous matrix and the indicator molecules may be attached to the immobilized macromolecule. The density of reactive groups can be directly controlled according to the amount added to the sol-gel, or by other methods, including partial blocking of reactive groups with capping reagents. The amount of reactive sites is also subject to control by adding additional polymers to the sol-gel.

DETAILED DESCRIPTION OF THE INVENTION

The invention provides a sensor comprised of a nonenzymatic macromolecule is immobilized, via entanglement, entrapment or otherwise, in sol-gel glass. The nonenzymatic sensor satisfies many of the needs left unmet by currently commercially available sensors. The invention provides a sensor that is stable at high temperatures, allowing it to be autoclaved or otherwise sterilized. A sensor according to the invention has a lifetime of months or years, can be cast into any size, shape, or cast into a thin film. The indicator element of the sensor will not leach out. Surface effects can be both overcome (where undesirable) and introduced (where desirable) according to the particular design of the sensor.

The sensor element is comprised of a sol-gel glass that has incorporated amongst or within its internal porous matrix an immobilized component, at least one type of nonenzymatic macromolecule to which an indicator is attached. The non-enzymatic macromolecule may be made from a variety of materials, however, the best results have been achieved with polyvinyl amine, polyallylamine, polyacrylic acid, and polyvinyl alcohol. Other natural or synthetic polypeptides may be used to form the non-enzymatic macromolecule. Sol-gels suitable for the invention include a variety of inorganic silica sol-gel glass precursors, including tetra-alkoxysilanes. Extended pH stability can be obtained by forming the sol-gels of other precursor compositions, leading to products such as zirconia or titania. Completely organic sol-gel glasses may also be prepared.

The non-enzymatic macromolecule is integrated into the porous matrix by being physically immobilized in the sol-gel. While the precise manner of immobilization is not known, the inventor believes that the macromolecule is somehow entangled or otherwise firmly fixed to the sol-gel, whether entrapped in the pores or otherwise.

At some point in the sensor formation, an indicator molecule is attached to the macromolecule. This indicator molecule attachment may occur before the macromolecule is immobilized in the sol-gel. Alternatively, indicator attachment may occur after the non-enzymatic macromolecule has been immobilized, and even after the sol-gel glass has been formed.

EXAMPLES

A. Preparation of phenol red-polyallyl amine adduct

Polyallylamine (mw 60,000) (25 mg) is dissolved in 1 ml of 1 molar pyridine-HCl buffer, pH 5.8. Carboxyphenol red (10 mg) is dissolved in 2 ml of the same buffer. The two solutions are combined, and to this is added 7 mg of 1-(3-dimethyl aminopropyl)-3-ethylcarbodiimide hydrochloride (EDC). The solution is stirred for approximately twelve to twenty four hours, generally being left to stir overnight. The supernatant is diluted and then dialyzed for several days against water and borate buffer, or purified by running through a size-exclusion chromatography column.

B. Incorporation of phenol red-polyallylamine in sol-gel glass

A sol-gel stock solution is prepared using 4.92 ml of tetramethoxysilane (TMOS), 1.13 ml of water and 0.073 ml of 0.04 molar HCl. This mixture is sonicated for 20 minutes, after which it becomes one-phase. Two (2) ml of the sol-gel stock solution, 2 ml of pH 6 phosphate, and 1 ml of solution containing the phenol red-polyallylamine adduct is mixed together and poured into a plastic petri dish. After gelation, the gel is cured for several (3–4) days, and then slowly dried over one week, the resulting slab of sol-gel glass shows the expected sensitivity: Under basic conditions, it is purplish-red and under acidic conditions it is yellow.

If the sensor is intended to be autoclaved or otherwise exposed to temperatures in excess of 120 degrees C., decomposition or oxidation of unreacted amine groups (and the concomitant color change that sometimes be perceived visually) can be avoided by capping any unreacted amine groups through treatment of the sensor with n-acetylimidazole for 12–24 hours at pH 8.5. The resulting sensor should be color stable before and after autoclaving.

C. Preparation of polyallylamine containing glass

Two (2) ml of the stock sol-gel solution is mixed with 2.5 ml of pH 6 phosphate (0.01 molar) and 0.5 ml of pH 6 aqueous solution of 20% polyallylamine. The mixture is poured into the wells of a microtitre plate and allowed to gel. After curing and drying, small discs (2–3 mm in diameter) of polyallylamine-containing glass are obtained.

The polyallylamine content, based on the theoretical $SiO_2$ content, is approximately 15%. This corresponds to approximately 1.5 milliequivalents of amine per gram of glass.

Similar glass can be made using smaller amounts of a polyallylamine-containing solution. Using 0.33 ml of the 20% polyallylamine solution results in a 10% polymer-in-glass composition. Using 0.03 ml results in a 1% polymer in glass composition.

D. Coupling of phenol red to polyallylamine glass

Carboxyphenol red, an indicating dye with a pendant carboxyl group, was coupled to the amine-containing glass under typical conditions using EDC. At pH 9.8, the glass was purple in color; at pH 4, it was yellow. The dye did not diffuse out of the glass even after autoclaving at 121° C.

The sol-gel glass can also be prepared with other monomers known to those practiced in the art, including TEOS and complexes of zirconium tetrapropoxide/acetylacetone.

Other polymers can be added to the sol-gel glass, including positively charged, such as polybrene; negatively charged, such as polyacrylic acid; and neutral, such as polyethylene glycol.

E. The Method

Generally, the method of making the sensor is comprised of a number of steps. In designing the sensor, at least three types of :materials must be selected: material for the sol-gel, the polymer, and the indicator. Suitable sol-gel precursors must be chosen, along with one or more types of macromolecules and indicator molecules which will perform under the expected conditions to be encountered by the sensor.

The method of making a sensor element according to the present invention comprising the steps of:

a) selecting a precursor composition capable of forming a sol-gel glass;

b) selecting at least one type of non-enzymatic macromolecule which has attached to it pre-determined indicator molecules;

c) making a sol from the precursors (from step a)

d) adding the macromolecule (from step b) to the sol (step c);

e) making a gel from the sol (product of step d);

f) making a glass from the sol-gel (product of step e).

The preferred time to add the macromolecule is during the sol stage. However, macromolecule may be added to precursors or at any time before the gel stage. The method is flexible with respect to the step at which the indicator or indicators may be added. Quite simply, an indicator can be bound to the macromolecule prior to mixing the macromolecule into the sol ingredients, or it can be added during or after the gel phase. Indicator can be added to a curing or fully cured sol-gel glass. Custom indicator design may be accomplished by adding different types of indicators or at different steps in the process. One indicator may be bound to the macromolecule prior to the sol phase, and another may be added at some later phase. Likewise, more than one type polymer can be added to the sol-gel and different polymers can be added at different stages in the process. For instance, one polymer may be added to the precursor composition. A different polymer, perhaps with a different indicator molecule already attached, can be added during the sol formation. The ratio of the various polymers and their respective indicators can be controlled.

Material selection may be governed by pragmatics such as low cost and ease of getting certain materials. Polyallylamine was selected by the inventor in consideration of these factors (easily obtained, reasonably priced) as well as the characteristic of having a large number of "handles" or reactive sites upon which to attach indicator molecules (i.e. 10–11 milliequivalents of amine per gram of polymer). The greater the density of indicator molecules, the more intense the color of the sensor. Other macromolecules suitable for sensors according to the invention include polyvinyl amine, polyacrylic acid, and polyvinyl alcohol. Theoretically, any natural or synthetic polypeptide may serve as the immobilized macromolecule. Sensors may also be designed that include more than one type of macromolecule and more than one type of indicator. These multi-indicator sensors could prove economical, allowing a single sensor to be used repeatedly for a range of indicator conditions, and to be sterilized without loss of performance.

What is claimed is:

1. A sensor element useful in making optical measurement wherein the sensor element comprises:
   a sol-gel glass;
   an immobilized macromolecule integrated within the sol-gel glass wherein the immobilized macromolecule is non-covalently bonded to the sol-gel and wherein it includes a chemically sensitive indicator material; and
   wherein the resulting sensor element performs at temperatures up to approximately 121 degrees C.

2. A sensor element as in claim 1 wherein the immobilized macromolecule is selected from a group consisting of: polyvinyl amine, polyallylamine, polyacrylic acid, polyvinyl alcohol.

3. A sensor element as in claim 1 wherein the immobilized macromolecule is a polypeptide.

4. A sensor element as in claim 1 wherein the immobilized macromolecule is comprised of a plurality of polymer types present in a pre-determined ratio in the sol-gel glass.

* * * * *